United States Patent [19]

Heller et al.

[11]  4,219,388
[45]  Aug. 26, 1980

[54] PROCESS FOR THE RECOVERY OF MALEIC ANHYDRIDE FROM DISTILLATION RESIDUES

[75] Inventors: Karl-Heinz Heller; Günther Lenz, both of Krefeld, Fed. Rep. of Germany

[73] Assignee: Bayer Aktiengesellschaft, Leverkusen, Fed. Rep. of Germany

[21] Appl. No.: 955,282

[22] Filed: Oct. 26, 1978

[30] Foreign Application Priority Data

Nov. 10, 1977 [DE] Fed. Rep. of Germany ....... 2750284

[51] Int. Cl.² ...................... B01D 3/10; C07D 307/89
[52] U.S. Cl. .................................. 203/61; 260/346.76
[58] Field of Search ........................ 260/346.76, 346.7; 203/61, 38, 91, 6, DIG. 25; 159/47 R

[56] References Cited

U.S. PATENT DOCUMENTS

| | | | |
|---|---|---|---|
| 2,670,355 | 2/1954 | Barsky et al. | 260/346.76 |
| 3,865,849 | 2/1975 | Garkish et al. | 260/346.76 |
| 3,965,126 | 6/1976 | Wirth et al. | 260/346.76 |
| 4,118,403 | 10/1978 | White | 260/346.76 |

FOREIGN PATENT DOCUMENTS 1807039  5/1970  Fed. Rep. of Germany ............ 203/61

*Primary Examiner*—Wilbur L. Bascomb, Jr.
*Attorney, Agent, or Firm*—Sprung, Felfe, Horn, Lynch & Kramer

[57] ABSTRACT

A process for the recovery of maleic anhydride from distillation residues containing the same is described whereby a residue containing phthalic anhydride is added to the residue of maleic anhydride prior to or after distillation of the maleic anhydride residue. By such a process maleic anhydride recovery is improved and the distillation residue remaining from distillation of the maleic anhydride out of the maleic anhydride residue remains removable by simple mechanical means from the distillation vessel.

12 Claims, No Drawings

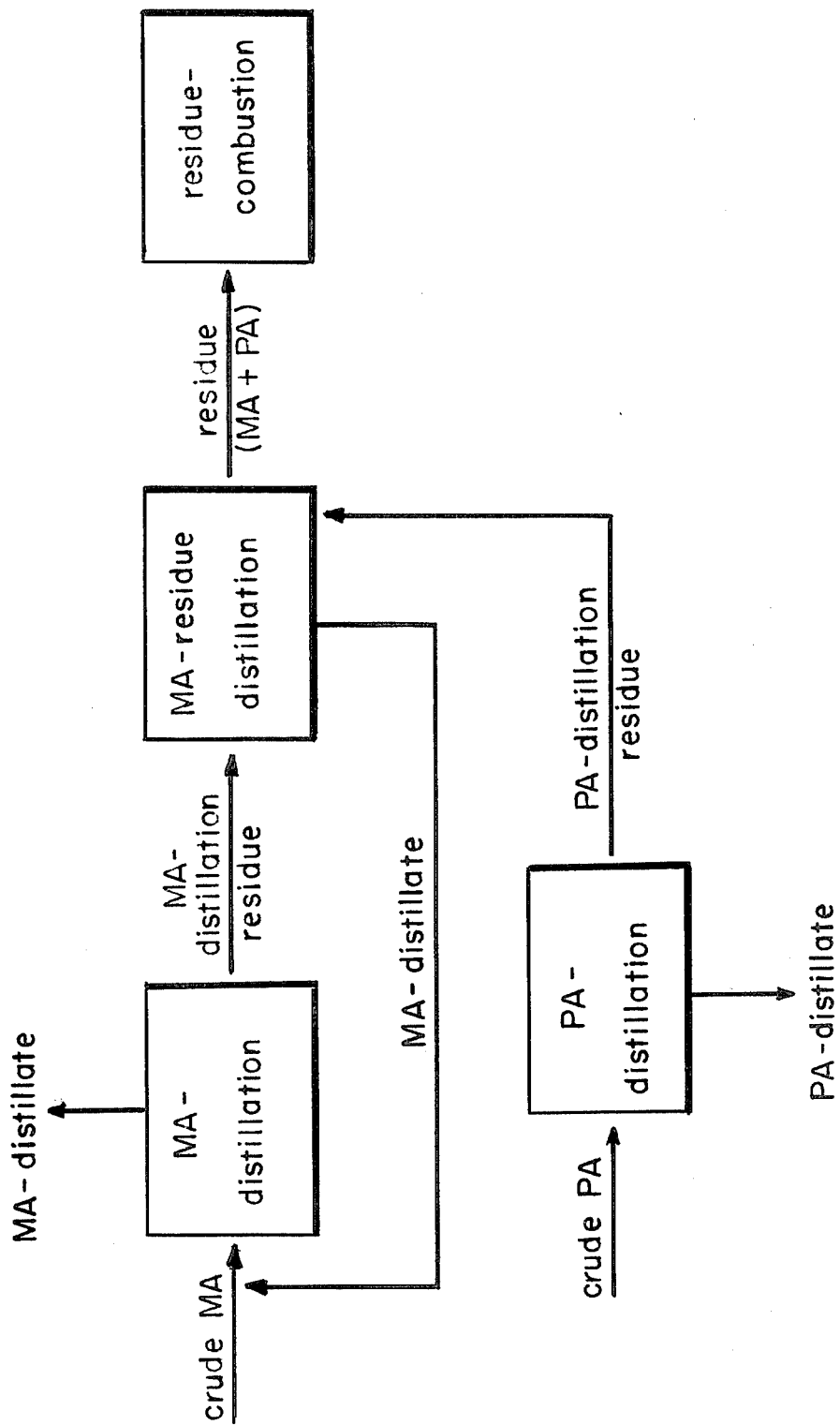

PROCESS FOR THE RECOVERY OF MALEIC ANHYDRIDE FROM DISTILLATION RESIDUES

The invention relates to a process for the recovery of maleic anhydride from distillation residues containing maleic anhydride, such as are obtained industrially during working up of crude maleic anhydride to pure maleic anhydride.

Thus a process is known, for example from German Offenlegungsschrift 2,061,335 and German Pat. No. 2,061,336, to obtain pure maleic anhydride from crude maleic anhydride which has been prepared by oxidation of benzene or $C_4$-hydrocarbons. In this process, after separating pure maleic anhydride, a residue which still contains maleic anhydride remains, from which maleic anhydride is recovered by distillation. It is also known, for example from U.S. Pat. Nos. 2,509,873, 2,770,630 and 2,989,545, to recover the maleic anhydride obtained as a by-product during the manufacture of phthalic anhydride, by catalytic oxidation of napthalene or o-xylene, from the phthalic anhydride off-gas wash water by dehydration and distillation. In this process, after separating pure maleic anhydride, a residue which still contains maleic anhydride is likewise obtained. However, it is not possible to recover almost completely the maleic anhydride contained in the distillation residues by these processes.

Experience has shown that the residue remaining after carrying out the distillation according to the state of the art still contains about 30 to 50% of maleic anhydride. This still considerable content of maleic anhydride is necessary to keep the residue sufficiently capable of flow, so that it can be drained or discharged from the distillation unit. If the residue is distilled too extensively, the viscosity and the content of crystalline fumaric acid increase to such an extent that it is no longer possible to remove the residue in the liquid state from the distillation unit and to pass it to a particularly advantageous way of destruction, for example by combustion in the liquid state.

Combustion of the residue in the liquid state is the most favorable method for its disposal, both for reasons of cost and for reasons of environmental protection, since other conceivable methods, such as, for example, dissolving the residue in water and disposing of the effluent in a biological treatment plant, or by combustion of the aqueous solution, or by allowing the residue to solidify and dumping or burning it in the solid state, after crushing it, are in some cases associated with considerable costs or a pollution of the environment cannot be completely avoided employing these methods. A considerable proportion (2 to 8%) of the amount of maleic anhydride produced is accordingly destroyed together with the distillation residue during the process carried out according to the state of the art, and thus the yield is reduced.

Now a process has been found for the recovery of maleic anhydride from maleic anhydride distillation residues, which is characterized in that maleic anhydride is distilled out of the distillation residue, containing maleic anhydride, in a distillation unit, a residue containing phthalic anhydride being added to the distillation residue, before or after the distilling-out step, in an amount such that the weight ratio of residue containing phthalic anhydride to maleic anhydride residue which has been subjected to the distilling-out step is 0.3 to 1.5:1, and the resulting mixture of residues is then discharged from the bottom of the distillation unit.

In general, maleic anhydride is distilled out of the distillation residue, containing maleic anhydride, down to a final content of less than 15% by weight of maleic anhydride, preferably less than 5% by weight of maleic anhydride.

The phthalic anhydride residue to be added to the maleic anhydride distillation residue, before or after the distilling-out step, according to the invention, is the mixture of the first runnings and of the bottom product discharged from the bottom of the main column, obtained during the distillation of crude phthalic anhydride to give pure phthalic anhydride in a distillation unit usually consisting of a first runnings column and a main column. The mixture used according to the invention, called the phthalic anhydride residue, is essentially composed of about 30 to 80% of phthalic anhydride, 10 to 40% of benzoic acid, 3 to 8% of maleic anhydride and 10 to 20% of higher-boiling, in some cases resinous substances, and has a solidification range from about 100° to 130° C.

The phthalic anhydride residue is of low viscosity at temperatures above 130° C. and contains virtually no solid constituents. It is miscible with the maleic anhydride distillation residue in all proportions.

The phthalic anhydride residue is a waste product without any value, which is formed during the manufacture of phthalic anhydride. It is usually burnt in an installation for the combustion of liquid waste materials.

Using the phthalic anhydride residue as a diluent for the maleic anhydride residue, on the one hand a maleic anhydride is obtained during the distillation of the residue which can be easily processed to give an end product of the purity required and on the other hand the viscosity of the residue mixture which is essentially free from maleic anhydride becomes so low and the mixture becomes so easily manageable that it can be discharged out of the distillation unit so that it can be fed to a combustion installation for liquid waste materials without difficulties.

BRIEF DESCRIPTION OF DRAWING

The drawing is a flow diagram of a suitable method for carrying out the invention and recovering maleic anhydride.

The process according to the invention may be carried out, for example, as follows. During the distillation, carried out continuously or discontinuously, of a crude maleic anhydride solution, which in addition to about 60 to 80% of maleic anhydride contains about 15 to 40% of the entraining agent used during the dehydration of the aqueous maleic anhydride solution, for example o-xylene, as well as relatively small amounts of resinous substances and sparingly soluble fumaric acid, after distilling off of the entraining agent and most of the maleic anhydride about 5 to 15%, relative to maleic anhydride distilled off, of a residue remain, which in addition to the high-boiling in some cases resinous constituents and crystalline fumaric acid also contains about 30 to 90% of maleic anhydride. This residue is conveyed through a heated pipeline by means of a suitable pump or by reduced pressure into a discontinuously operated unit for distilling the residue. This distillation unit consists of a still equipped with a stirrer, heating device, vapour tube, condenser cooled with warm water, receiver and vacuum system. In this distillation still, the phthalic anhydride residue is added to the maleic anhydride distillation residue, either directly by means of a heated pipe from the residue storage tank of a phthalic anhydride distillation installation, or by means of a conveying container which can be heated, in such an amount that the ratio of phthalic anhydride residue to maleic anhydride residue is about 0.3 to 1.2:1. In most cases a ratio of 0.4 to 0.7:1 is sufficient. After mixing the two residues, the maleic anhydride contained in the mixture is distilled off under a pressure in the range from about 150 to 2 mm Hg, preferably 70 to 10 mm Hg, and at a sump temperature in the range from about 100°–180° C., preferably 140° to 170° C. Analysis of the bottom product shows a residual content of maleic anhydride of less than 5%. The residue which is essentially free from maleic anhydride and which has a low viscosity at temperatures in the range from about 130°–180° C., is discharged through a bottom outlet in the distillation still into a conveying container, which can be heated, and is fed to a combustion installation for liquid waste materials.

The maleic anhydride distilled off is pumped back into the intermediate storage container for crude maleic anhydride and is distilled in the next batch to give pure maleic anhydride.

The yield of the working-up process for maleic anhydride is increased by about 5 to 8% by the process described, according to the invention.

In a further embodiment of the process according to the invention, the residue, which is obtained during the continuous or discontinuous distillation of the crude maleic anhydride solution and which contains still about 30 to 90% of maleic anhydride is conveyed into the unit already described for distilling the residue and, without any addition, is subjected to the distillation step under the conditions indicated above until no further maleic anhydride distills over. As a result of its relatively high content of solid fumaric acid and of resinous substances, the remaining residue, containing less than 5% of maleic anhydride, has very poor flow properties. The phthalic anhydride residue is thereafter added to this residue as described above, at a temperature of about 160° C., in an amount such that the weight ratio of phthalic anhydride residue to maleic anhydride residue which has been subjected to the distillation step is about 0.5 to 1.5:1. This mixture, which has now very good flow properties, is discharged at temperatures in the range from about 130° to 180° C. and is fed to the combustion unit by means of a conveying container which can be heated.

The maleic anhydride distilled off is pumped to the crude maleic anhydride stage of the working-up process.

Economic advantages of the process according to the invention accordingly result, on the one hand, in increased yields of maleic anhydride, indicated by the amount of maleic anhydride recovered from the distillation residue, and, on the other hand, by a reduced amount of residue to be incinerated, also shown by the amount of maleic anhydride recovered. The cost of the phthalic anhydride residue added can be neglected since it is a waste product which in all cases has to be burnt anyway or destroyed in another manner, in some cases causing additional costs.

The following examples serve to illustrate the process according to the invention in more detail. In the examples, maleic anhydride is referred to as MA and phthalic anhydride in referred to as PA.

EXAMPLE 1

(a) A reaction gas containing MA is produced by oxidizing a $C_4$-hydrocarbon mixture containing n-butenes by atmospheric oxygen on a fixed bed catalyst arranged in a multi-tube reactor. An approximately 40% aqueous maleic acid solution is obtained in a gas scrubber by absorption and hydration of the MA contained in the gas stream. By dehydrating this maleic acid solution in a dehydration column, using o-xylene as an entraining agent, a mixture consisting of 80% of MA, about 18% of o-xylene and, in addition to other by-products, which in some cases are resinous, of small amounts of fumaric acid is obtained as a crude MA solution.

This crude MA solution is fractionated in a distillation unit, operated batchwise, essentially consisting of a distillation still equipped with stirrer, a tray column, condenser, receiver and vacuum system, pure MA being obtained as the main product, in addition to first runnings and intermediate runnings. A mixture remains as the distillation residue in an amount of 12%, relative to pure MA produced, which according to analysis has, for example, the following composition: 52% of MA, 30% of resins and 18% of fumaric acid.

This residue is discharged at a temperature of 155° C. into a conveying container which can be heated.

(b) 3 tons of the MA residue are now fed into the unit for distilling the residue. The unit for distilling the residue consists of a 10 $m^3$ still equipped with a steam heating device of 16 bar pressure steam, stirrer, a simple fractionator without a column, a condenser, product receivers and a vacuum system. 2.5 tons of PA residue from the residue container of a PA distillation installation are added to the MA residue by means of a conveying container which can be heated. The PA residue has the following composition: 62% of PA, 23% of low-boiling impurities, essentially benzoic acid, and about 15% of higher-boiling substances, some of which are resinous.

1.37 tons of MA, containing only slight amounts of benzoic acid and PA as impurities (about 4%), are distilled off under a vacuum of 30 mm Hg at a sump temperature of 130°–160 ° C., whilst stirring. The residue which remains has a residual MA content of 4.6%. It is discharged without difficulties through a bottom outlet in the distillation still into a conveying container which can be heated. This residue can be incinerated without difficulties in a combustion installation for liquid waste materials.

The MA distilled off is pumped out of the distillation receiver into the intermediate storage container for crude MA. The MA yield of the entire process is increased by 5.5%.

EXAMPLE 2

5 tons of the MA distillation residue, with an MA content of 52%, obtained according to Example 1(a) during the preparation of MA from a $C_4$ mixture are subjected to a distilling-out step in the unit, described in Example 1(b), for distilling the residue, under a vacuum of 20 mm Hg and at sump temperatures in the range from 130° to 170° C., until no further MA distills over 2.5 tonnes of MA, essentially free from impurities, are obtained.

2 tons of PA residues of the composition indicated in Example 1(b) are added at a temperature of 160° C. to the remaining distillation residue which has a residual MA content of about 4%. After mixing at 160° C. for a short time, the residual mixture can be discharged without difficulties into a heated conveying container and can be fed to the incinerator. The MA distilled off (6% of the amount of MA produced) is recycled to the intermediate container for crude MA.

EXAMPLE 3 (comparison example)

A further amount of 5 tons of the MA distillation residue obtained according to Example 1(a), with an MA content of 52%, is fed into the unit, described in Example 1(b), for distilling the residue. The residue is distilled under a vacuum of 20 mm Hg and at sump temperatures in the range from 130° to 170° C. until no further MA distils over. The residue remaining in the vessel still contains about 5% of MA. It has poor flow properties and has a high concentration of crystalline fumaric acid. Only a small amount of the residue can be discharged from the distillation still at temperatures from 160° to 170° C. since the outlet becomes blocked. It is not possible to feed the portion discharged to the combustion unit by means of conveying containers and heated lines because of blockages and for lack of flow capability.

EXAMPLE 4

The reaction gas produced in a phthalic anhydride production installation by catalytic oxidation of o-xylene by atmospheric oxygen is scrubbed in a gas washer, after desublimation of the phthalic anhydride contained therein which is the main product of the process. An approximately 40% maleic acid solution is obtained by absorption in water and hydration of the MA contained in the gas stream. MA is formed as a by-product of the o-xylene oxidation reaction. A crude MA solution which contains about 80% of MA, 18% of o-xylene and, in addition to other by-products, some of which are resinous, small amounts of fumaric acid and phthalic acid, is obtained from this maleic acid solution in a dehydration column, using o-xylene as the entraining agent.

This crude MA solution is distilled batchwise, as described in Example 1(a), to give pure MA. A mixture remains as the distillation residue in an amount of 15%, relative to pure MA produced, which has approximately, the following composition: 61% of MA, 25% of resins, 12% of fumaric acid and 2% of phthalic anhydride.

This residue is discharged at a temperature of 160° C. into a conveying container which can be heated.

5 tons of this residue are subjected to the distillation step of the unit, described in Example 1(b), for distilling the residue, under a vacuum of 25 mm Hg and at sump temperatures from 130° to 180° C. until no further MA distils over. 2.95 tons of MA are obtained.

1.5 tons of PA residue of the composition indicated in Example 1(b) are added at a temperature of 170° C. to the remaining distillation residue, which has a residual MA content of 4.8%. After mixing at 160° C. for a short time, the residue mixture can be discharged completely into a conveying container which can be heated, and can be fed to the combustion unit.

What is claimed is:

1. A process for the recovery of maleic anhydride from a distillation residue containing the same which comprises subjecting said distillation residue to distillation to distill-out maleic anhydride, adding a residue containing phthalic anhydride to the distillation residue containing maleic anhydride before or after maleic anhydride is distilled thereoff in an amount such that the weight ratio of residue containing phthalic anhydride to residue containing maleic anhydride which has been or is to be subjected to distillation is 0.3 to 1.5:1 and discharging the resultant residue from the bottom of the distillation unit.

2. A process according to claim 1 wherein maleic anhydride is distilled-out of a distillation residue containing the same and down to a final content of less than 15% by weight of maleic anhydride.

3. A process according to claim 1 wherein distillation is effected at a temperature in the range of from 100° to 180° C. and at a pressure of 150 to 2 mm Hg.

4. A process according to claim 1 wherein the residual mixture is discharged from the bottom of the distillation unit at a temperature of 130° to 180° C.

5. A process according to claim 1 wherein the residue containing the phthalic anhydride is added to the residue containing the maleic anhydride prior to distilling-off the maleic anhydride.

6. A process according to claim 1 wherein the maleic anhydride is distilled-off from the residue containing the maleic anhydride prior to addition of the residue containing phthalic anhydride.

7. A process according to claim 5 wherein said residue containing phthalic anhydride comprises 30 to 80% phthalic anhydride, 10 to 40% benzoic acid, 3 to 8% maleic anhydride and 10 to 20% higher boiling components, the solidification point of said residue being from about 100° to 130° C.

8. A process according to claim 6 wherein said residue containing phthalic anhydride comprises 30 to 80% phthalic anhydride, 10 to 40% benzoic acid, 3 to 8% maleic anhydride and 10 to 20% higher boiling components, the solidification point of said residue being from about 100° to 130° C.

9. A process according to claim 7 wherein said residue containing phthalic anhydride is one obtained as a waste product in the manufacture of phthalic anhydride.

10. A process according to claim 8 wherein said residue containing phthalic anhydride is one obtained as a waste product during the manufacture of phthalic anhydride.

11. A process according to claim 7 wherein the residue containing phthalic anhydride is present in an amount corresponding to a ratio to the residue containing maleic anhydride of 0.4 to 1.5:1.

12. A process according to claim 8 wherein the weight ratio of residue containing phthalic anhydride to residue containing maleic anhydride which has been subjected to distillation is 0.4 to 1.5:1.

* * * * *